United States Patent [19]
Hausheer et al.

[11] Patent Number: 5,935,967
[45] Date of Patent: Aug. 10, 1999

[54] PHARMACEUTICAL FORMULATIONS OF HIGHLY LIPOPHILIC CAMPTOTHECIN DERIVATIVES

[75] Inventors: Frederick H. Hausheer, Boerne; Kochat Haridas, San Antonio; Dhanabalan Murali, San Antonio; Dasharatha Gauravaram Reddy, San Antonio, all of Tex.

[73] Assignee: BioNumerik Pharmaceuticals, Inc., San Antonio, Tex.

[21] Appl. No.: 09/009,067

[22] Filed: Jan. 20, 1998

Related U.S. Application Data

[63] Continuation-in-part of application No. 08/667,424, Jun. 21, 1996, Pat. No. 5,880,133, which is a continuation-in-part of application No. 08/461,385, Jun. 5, 1995, Pat. No. 5,726,181.

[51] Int. Cl.⁶ .................................................. A61K 31/475
[52] U.S. Cl. ............................................. 514/283; 514/423
[58] Field of Search ...................................... 514/283, 423

[56] References Cited

U.S. PATENT DOCUMENTS

| | | | |
|---|---|---|---|
| 5,422,361 | 6/1995 | Munayyer et al. | 514/408 |
| 5,447,936 | 9/1995 | Hausheer et al. | 514/283 |
| 5,468,754 | 11/1995 | Hausheer et al. | 514/283 |
| 5,573,781 | 11/1996 | Brown et al. | 424/484 |

*Primary Examiner*—Rebecca Cook
*Attorney, Agent, or Firm*—Thomas J. Dodd

[57] ABSTRACT

Pharmaceutical formulations of highly lipophilic, poorly water soluble derivatives of Camptothecin are disclosed. The formulations include an effective amount of the HLCD dissolved or suspended in an appropriate amount of N-methyl-2-pyrrolidinone (NMP), and one or more pharmaceutically acceptable excipients.

8 Claims, No Drawings

PHARMACEUTICAL FORMULATIONS OF HIGHLY LIPOPHILIC CAMPTOTHECIN DERIVATIVES

This application is a continuation-in-part of U.S. patent application, Ser. No. 08/667,424, filed Jun. 21, 1996, now U.S. Pat. No. 5,880,133, which is a continuation-in-part of U.S. patent application, Ser. No. 08/461,385, filed Jun. 5, 1995, now U.S. Pat. No. 5,726,181.

FIELD OF THE INVENTION

This invention relates to pharmaceutical formulations of certain novel, highly lipophilic camptothecin (CPT) derivatives. The formulations include a quantity of the CPT derivative dissolved or suspended in a primary solvent, N-methylpyrrolidin-2-one (NMP).

BACKGROUND OF THE INVENTION

The lactone form of camptothecin and nearly all derivatives thereof are highly lipophilic, poorly water soluble compounds (HLCDs). Typically, less than 5 micrograms of the lactone form of CPT (and many of its derivatives) will dissolve in 1 milliliter of water. The carboxylate form of CPT, with its opened E-ring has a much greater water solubility. However, the carboxylate form of the drug possesses much lower antineoplastic activity and has exhibited higher toxicity when administered to patients with cancer.

Due to the poor water solubility of lactone CPT and derivatives, which limits the ability to readily administer HLCDs in a clinically practical manner, a great deal of research has been conducted to develop lactone CPT derivatives which possess greater water solubility. This research has produced compounds such as CPT-11 (7-ethyl-10-[4-(1-piperidino)-1-piperidino] carbonyloxy camptothecin also referred to as Irinotecan or Camptosar™), which was approved for use in the United States in 1996, and Topotecan (9-dimethylaminomethyl-10-hydroxy camptothecin), also recently approved for use as a cancer chemotherapeutic agent.

CPT-11 is a water soluble prodrug for the highly active, highly toxic, highly lipophilic CPT derivative, SN38 (10-hydroxy-7-ethyl-CPT). CPT-11 is an inactive compound, and requires activation by a putative carboxylesterase enzyme to the active SN38 species. It is also known that SN38 can undergo an additional glucuronidation reaction, in vivo, and that the SN38-glucuronide species may be highly toxic to normal, healthy cells, and has little antitumor activity.

Lipid soluble CPT derivatives have heretofore presented problems of formulation, administration and delivery to the patient. Because of CPT's poor water solubility, other solvents, such as sodium hydroxide, had to be employed in order to effectively deliver the drug as a solution, rather than a suspension, to the patient.

Some efforts to develop alternative formulations of highly lipophilic, poorly water soluble derivatives of Camptothecin (HLCDs) are disclosed in U.S. Pat. Nos. 5,447,936; 5,633,260; 5,674,273; and 5,674,274. The disclosures of these patents, commonly owned by the assignee of this invention, disclose the use of alternative solvents, dimethylacetamide (DMA) and dimethylisosorbide (DMI). U.S. patent application Ser. Nos. 08/461,385, filed Jun. 5, 1995, and 08/667, 424, filed Jun. 21, 1996, disclose the use of N-methyl-pyrrolidin-2-one (NMP) as an alternative solvent for a number of HLCD formulations.

SUMMARY OF THE INVENTION

The formulations of this invention include as the primary formulation solvent the compound N-methylpyrrolidin-2-one, also referred to as N-methylpyrrolidinone, or simply, NMP. The solubility of highly lipophilic, poorly water soluble camptothecin derivatives is increased to between approximately 15.0 and 25.0 mg/mL in NMP, which allows for much more concentrated drug solutions to be prepared in advance of formulating. The resulting higher drug concentration attained by the instant invention allows greater utility for preparing oral and parenteral formulations.

The preferred formulations of this invention include the following: [a] an HLCD of formula I; [b] NMP; and optionally include [c] polyethylene glycol (PEG) or propylene glycol; [d] an acid; [e] a non-ionic surfactant; and [f] a low molecular weight alcohol. In addition, certain formulations may also include [g] a heavy oil, such as epoxylated castor oil; [h] glycerol; and [i] taurocholic acid or a pharmaceutically acceptable salt thereof, or a similar intestinal absorption enhancing agent.

The formula I HLCDs all have the following structure:

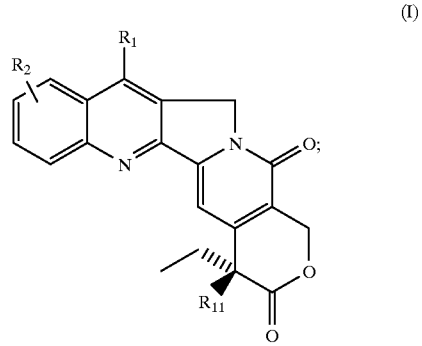

(I)

wherein: $R_1$ is hydrogen; acyl, $C_2$–$C_8$ alkenyl, or $C_2$–$C_8$ alkynyl, optionally substituted by one or more halogen atoms or $OR_4$ or lower alkyl for a corresponding hydrogen atom therein; oxo; aryl; arylalkyl; arylalkenyl; arylalkynyl; heterocycle; $SR_5$; —S(O)-lower alkyl; -lower alkyl—P(O) $R_6R_7$, or X—($C_0$–$C_6$ alkyl, $C_0$–$C_8$ alkenyl, or $C_0$–$C_8$ alkynyl)-$SiR_8R_9R_{10}$;

$R_2$ is hydrogen, halo, lower alkyl, amino or nitro, provided that $R_1$ and $R_2$ are not both hydrogen;

$R_4$ is hydrogen or lower alkyl;

$R_5$ is hydrogen or lower alkyl;

$R_6$ and $R_7$ are each individually hydrogen or lower alkyl;

$R_8$, $R_9$ and $R_{10}$ are each individually hydrogen or lower alkyl;

$R_{11}$ is hydrogen, hydroxy or lower alkoxy; and

X is sulfur or X is absent; or a pharmaceutically acceptable salt thereof;

The formula I compounds are disclosed and claimed in the assignee's co-pending application, Ser. No. 60/024,171, filed Aug. 19, 1996.

The formulations of this invention contain a high concentration of a HLCD (the "active ingredient") due to the unpredictably high solubility of the compounds in NMP. This allows a lower solvent volume delivery to the patient in delivering the same amount of active ingredient, which in turn results in reduced risk of toxicity and greater patient acceptance.

The formulations of this invention can be tailored for various types of delivery, including parenteral, topical, subcutaneous and oral, among others. Specific examples of oral and parenteral formulations are given in the detailed description which follows.

The formulations of this invention can be tailored for all types of delivery, with the preferred forms of delivery being parenteral and oral. Parenteral formulations are generally administered as a solution, with the active ingredient completely dissolved in the liquid carrier, and maintaining a solution quality after final dilution. Oral formulations may be administered in any acceptable form, with the active ingredient dissolved in the liquid carrier, or held in suspension therewith.

Parenteral formulations are designed for delivery by any acceptable route, with the most preferred routes being intravenous, intrathecal, intracranial, intraperitoneal, intratumoral, and others. The most preferred parenteral formulations include an effective amount of the active ingredient, with an effective amount defined as that amount of drug which elicits a therapeutic response from the patient.

An effective amount of the active ingredient of the formula I compounds ranges from 0.005 mg/kg to 2.0 mg/kg, with the preferred range 0.01 mg/kg to 0.5 mg/kg. Typically, parenteral formulations of drug are shipped in concentrated solution form and diluted at the place of delivery just prior to administration to the patient. A typical final dilution is between 1:1 and 200:1 ratio of water:concentrated solution, with most preferred final dilution between 5:1 and 100:1. Simple calculations utilizing the preferred dilution factor and the effective dosage will determine the desired effective amount of active ingredient in the concentrate.

Typical oral formulations of drug may be dissolved or suspended in solution, or may consist of the active ingredient mixed with a solid filler. Oral formulations may be encapsulated within a digestible carrier such as hard or soft gelatin capsules, or may be self-contained in pill or caplet form, with or without an enteric coating. Oral formulations of drug are typically not diluted or otherwise altered after manufacture and shipping.

Within the context of this specification, the term "pharmaceutically acceptable" means a substance which is acceptable for administration to mammals, particularly human beings, with little or no individual or cumulative toxicity. Pharmaceutically acceptable excipients, diluents and carriers are defined to be those substances which are substantially inert with respect to the active ingredient, and which do not mediate adverse physical effects in the patient.

Preferred formulations according to this invention include one or more pharmaceutically acceptable excipients, diluents, and/or carriers. In parenteral formulations, preferred excipients include a pharmaceutically acceptable acid, which is employed primarily to lower the pH of the final formulation. Acidic pH enables the active CPT ingredient to remain in the more active lactone form, as opposed to the much less active carboxylate anion.

Other preferred excipients in parenteral formulations may include a glycol, a surfactant, a low molecular weight alcohol, an oil, glycerol, and others.

Oral formulations may include any or all of the above excipients, and will optionally include an intestinal absorption enhancing agent, such as taurocholic acid, and one or more solid fillers, such as starch, dextrose, or the like.

Preferred excipients, diluents and fillers are set forth below. In parenteral formulations, the preferred acid is either a mineral acid, such as hydrochloric acid or phosphoric acid, or an organic acid, such as tartaric acid, lactic acid, citric acid, ascorbic acid, gluconic acid, fumaric acid, maleic acid, and others. The most preferred acids from each group are hydrochloric acid and citric acid.

Preferred glycols include both propylene glycols and various polyethylene glycols (PEG), such as PEG 200, PEG 300, and PEG 400. Preferred surfactants include polysorbates, such as polysorbate-80. Other excipients which may be employed as surfactants include the high molecular weight oils, such as epoxylated castor oils, most notably Cremaphor®.

Low molecular weight alcohols suitable for use with the formulations include both aliphatic alcohols, most preferably ethyl alcohol, and aromatic alcohols, most preferably benzyl alcohol, and combinations of aliphatic and aromatic alcohols.

Preferred oral formulations may also include quantities of glycerol and/or an intestinal absorption enhancing agent such as taurocholic acid, or a salt thereof, or another bile acid.

The following table illustrates the preferred quantities of each of the preferred ingredients in both parenteral and oral formulations. In each case, the active ingredient is defined as a compound of Formula I, above.

TABLE 1

Component Parts For Parenteral Formulation

| Ingredient | Parts By Weight |
| --- | --- |
| Active Ingredient | 1 |
| NMP | 25 to 10,000 |
| Ethyl Alcohol | 0 to 5,000 |
| Benzyl Alcohol | 0 to 5,000 |
| Acid | 100 to 5,000 |
| PEG 400 | 100 to 10,000 |
| Cremaphor | 100 to 10,000 |
| Polysorbate 80 | 100 to 10,000 |

TABLE 2

Component Parts For Oral Formulation

| Ingredient | Parts By Weight |
| --- | --- |
| Active Ingredient | 1 |
| NMP | 25 to 10,000 |
| Ethyl Alcohol | 0 to 5,000 |
| Benzyl Alcohol | 0 to 5,000 |
| Acid | 100 to 5,000 |
| PEG 400 | 100 to 10,000 |
| Cremaphor | 100 to 10,000 |
| Polysorbate 80 | 100 to 10,000 |
| Glycerol | 0 to 2.5 |
| Taurocholic Acid | 1 to 10 |

As noted above, oral formulations may be, and preferably are, encapsulated within a swallowable carrier, such as a soft or hard gelatin capsule, or the like. Further, while parenteral formulations are preferably in solution phase, with the active ingredient completely dissolved in the liquid, oral formulations may include either solutions or suspensions of the active ingredient.

The process for preparing the preferred formulations vary. Generally, in parenteral formulations the primary solvent and the excipients are prepared first by mixing in a preferred order, to ensure complete dissolution of the solid excipients. Active ingredient is then added and dissolved in the solvent/excipient mixture, with the amount of active ingredient to be added corresponding to the desired final concentration of the formulation. As noted above, the formulation at this stage is referred to as the concentrated formulation, to be subject to final dilution at the site of administration, normally a hospital or similar health care facility.

Oral formulations are prepared in similar fashion, except that these are preferably shipped as finished products, ready for administration without further dilution or addition of other materials. Neat formulations of active ingredient and NMP may also be prepared in various concentrations.

The above description is not to be considered as limiting the invention in any way, with the scope of the invention defined by the following claims.

What is claimed is:

1. A pharmaceutical formulation comprising an effective amount of a camptothecin derivative having the formula:

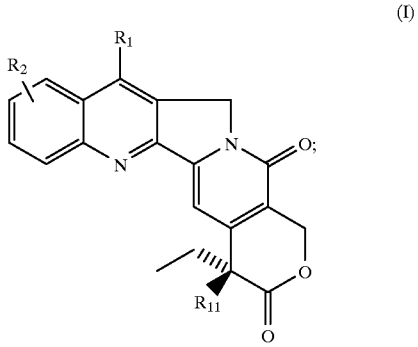

(I)

wherein:

$R_1$ is hydrogen; acyl, $C_2$–$C_8$ alkenyl, or $C_2$–$C_8$ alkynyl, optionally substituted by one or more halogen atoms or $OR_4$ or lower alkyl for a corresponding hydrogen atom therein; aryl; arylalkyl; arylalkenyl; arylalkynyl; heterocycle; $SR_5$; —S(O)-lower alkyl; -lower alkyl—P(O)$R_6R_7$, or X—($C_0$–$C_6$ alkyl, $C_0$–$C_8$ alkenyl, or $C_0$–$C_8$ alkynyl)-$SiR_8R_9R_{10}$;

$R_2$ is hydrogen, halo, lower alkyl, amino or nitro, provided that $R_1$ and $R_2$ are not both hydrogen;

$R_4$ is hydrogen or lower alkyl;

$R_5$ is hydrogen or lower alkyl;

$R_6$ and $R_7$ are each individually hydrogen or lower alkyl;

$R_8$, $R_9$ and $R_{10}$ are each individually hydrogen or lower alkyl;

$R_{11}$ is hydrogen, hydroxy or lower alkoxy; and

X is sulfur or X is absent; or a pharmaceutically acceptable salt thereof;

and a volume of N-methylpyrrolidin-2-one sufficient to form a solution or suspension with the formula I compound.

2. The pharmaceutical formulation of claim 1, and further comprising a quantity of hydrochloric acid, phosphoric acid, tartaric acid, lactic acid, citric acid, ascorbic acid, gluconic acid, fumaric acid, or maleic acid in sufficient quantity to lower the pH of the formulation between 2.0 to 6.0.

3. The pharmaceutical formulation of claim 2 wherein said formulation further comprises one or more pharmaceutically acceptable excipients, diluents or carriers.

4. The pharmaceutical formulation of claim 3 wherein the one or more pharmaceutically acceptable excipients are selected from the group consisting of ethyl alcohol or benzyl alcohol, a glycol polymer, a non-ionic surfactant, a heavy oil, glycerol, and an intestinal absorption enhancing ingredient.

5. The pharmaceutical formulation of claim 4 wherein said excipient is a glycol which is polyethylene glycol.

6. The pharmaceutical formulation of claim 5 wherein said excipient is a polyethylene glycol which is PEG 200, PEG 300 or PEG 400, or a combination thereof.

7. The pharmaceutical formulation of claim 4 wherein said excipient is a non-ionic surfactant which is a polysorbate.

8. The pharmaceutical formulation of claim 4 wherein said excipient is an intestinal absorption enhancing agent which is taurocholic acid, or a pharmaceutically acceptable salt thereof.

* * * * *